(12) United States Patent
Woodard et al.

(10) Patent No.: US 9,329,149 B2
(45) Date of Patent: May 3, 2016

(54) WIRELESS CHEMICAL SENSOR AND SENSING METHOD FOR USE THEREWITH

(71) Applicant: The United States of America as represented by the Administrator of the National Aeronautics and Space Administration, Washington, DC (US)

(72) Inventors: Stanley E. Woodard, Hampton, VA (US); Donald M. Oglesby, Hertford, VA (US); Bryant D. Taylor, Smithfield, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 106 days.

(21) Appl. No.: 14/215,793

(22) Filed: Mar. 17, 2014

(65) Prior Publication Data

US 2014/0199774 A1    Jul. 17, 2014

Related U.S. Application Data

(62) Division of application No. 12/463,475, filed on May 11, 2009, now Pat. No. 8,673,649.

(60) Provisional application No. 61/051,841, filed on May 9, 2008.

(51) Int. Cl.
*G01N 25/18*    (2006.01)
*G01N 27/26*    (2006.01)
*G01N 27/02*    (2006.01)
*G01N 27/12*    (2006.01)

(52) U.S. Cl.
CPC .............. *G01N 27/26* (2013.01); *G01N 27/021* (2013.01); *G01N 27/122* (2013.01)

(58) Field of Classification Search
None
See application file for complete search history.

(56) References Cited

U.S. PATENT DOCUMENTS

| | | | |
|---|---|---|---|
| 5,153,557 | A | 10/1992 | Partin et al. |
| 5,514,337 | A | 5/1996 | Groger et al. |
| 5,747,986 | A | 5/1998 | Hristoforou |
| 5,821,129 | A | 10/1998 | Grimes et al. |

(Continued)

FOREIGN PATENT DOCUMENTS

| | | |
|---|---|---|
| WO | 2004091396 A2 | 10/2004 |
| WO | 2007072243 A1 | 6/2007 |

OTHER PUBLICATIONS

Keat Ghee Ong, Kefeng Zeng, and Craig A. Grimes, "A Wireless, Passive Carbon Nanotube-Basad Gas Sensor," IEEE Sensors Journal, Apr. 2002, pp. 82-88, vol. 2, No. 2.

(Continued)

*Primary Examiner* — Robert Xu
(74) *Attorney, Agent, or Firm* — Robin W. Edwards

(57) ABSTRACT

A wireless chemical sensor includes an electrical conductor and a material separated therefrom by an electric insulator. The electrical conductor is an unconnected open-circuit shaped for storage of an electric field and a magnetic field. In the presence of a time-varying magnetic field, the first electrical conductor resonates to generate harmonic electric and magnetic field responses. The material is positioned at a location lying within at least one of the electric and magnetic field responses so-generated. The material changes in electrical conductivity in the presence of a chemical-of-interest.

12 Claims, 4 Drawing Sheets

(56) References Cited

U.S. PATENT DOCUMENTS

| | | |
|---|---|---|
| 6,359,444 B1 | 3/2002 | Grimes |
| 6,397,661 B1 | 6/2002 | Grimes et al. |
| 6,507,187 B1 | 1/2003 | Olivas et al. |
| 6,548,311 B1 | 4/2003 | Knoll |
| 6,639,402 B2 | 10/2003 | Grimes et al. |
| 6,823,720 B1 | 11/2004 | Adkins et al. |
| 6,948,388 B1 | 9/2005 | Clayton et al. |
| 7,086,593 B2 | 8/2006 | Woodard et al. |
| 7,159,774 B2 | 1/2007 | Woodard et al. |
| 7,176,344 B2 | 2/2007 | Gustafson et al. |
| 7,302,829 B2 | 12/2007 | Zribi |
| 8,673,649 B2 | 3/2014 | Woodard et al. |
| 2002/0166382 A1 | 11/2002 | Bachas et al. |
| 2006/0076236 A1 | 4/2006 | Shah et al. |
| 2006/0124740 A1 | 6/2006 | Woodard et al. |
| 2006/0292630 A1 | 12/2006 | Fukumoto |
| 2007/0181683 A1 | 8/2007 | Woodard et al. |

OTHER PUBLICATIONS

K.G. Ong, C.A. Grimes, C.L. Robbins, R.S. Singh, "Design and application of a wireless, passive, resonant-circuit environmental monitoring sensor," Sensors and Actuators A 93 (2001) pp. 33-43.

Birdsell, E. et al., "Wireless Chemical Sensors for High Temperature Environments", Solid-State Sensors, Actuators and Microsytems Workshop, Jun. 4-8, 2006, pp. 212-215, Hilton Head, South Carolina.

PCT International Search Report PCT/US2009/43415, pp. 1-8, Jun. 29, 2009.

WIRELESS CHEMICAL SENSOR AND SENSING METHOD FOR USE THEREWITH

This patent application is a divisional of U.S. patent application Ser. No. 12/463,475, filed May 11, 2009, which claims the benefit of priority to U.S. Provisional Patent Application Ser. No. 61/051,841, filed May 9, 2008. The contents of the foregoing applications are hereby incorporated by reference in their entirety.

ORIGIN OF THE INVENTION

This invention was made in part by an employee of the United States Government and may be manufactured and used by or for the Government of the United States of America for governmental purposes without the payment of any royalties thereon or therefore.

BACKGROUND OF THE INVENTION

1. Field of the Invention

This invention relates to chemical sensors. More specifically, the invention is a wireless chemical sensor that includes a material whose electrical conductivity changes in the presence of a chemical of interest, where such electrical conductivity changes a harmonic response of a spaced-apart electrically-unconnected geometric pattern that is electrically conductive.

2. Description of the Related Art

Chemical sensors have been employed for a large variety of applications such as bio-sensing, environmental analysis, food analysis, clinical diagnostics, drug detection, gas detection, toxicity detection, and detection of chemicals that could be used for warfare or terrorism. In one approach, sensors have a specific synthesized receptor that selectively binds with an analyte of interest. Another sensor approach is to have a specific chemical reactant react with a target reactant. Each approach produces a measurable change that is discernable via an electrical component such as a capacitor or resistor. Typically, the receptor/reactant must physically contact some part(s) of the electrical component(s). This can limit the number of applications that could utilize chemical sensors.

Chemical sensor innovation is driven by either the infrastructure innovations such as microelectromechanical or wireless sensors, or innovations/discoveries in chemistry such as the development of Carbon-60 that resulted in carbon nanotubes and the development of conductive polymers. Newer sensor baseline circuit designs include magnetic field response sensors that require no physical connections to a power source or acquisition hardware. For example, U.S. Pat. Nos. 7,086,593 and 7,159,774 disclose magnetic field response sensors designed as passive inductor-capacitor circuits and passive inductor-capacitor-resistor circuits that produce magnetic field responses whose harmonic frequencies correspond to states of physical properties of interest. A closed-circuit magnetic field response sensor is made by electrically connecting a spiral trace inductor to an interdigitated electrode capacitor or capacitor plates. A magnetic field response recorder wirelessly transmits a time-varying magnetic field that powers each sensor using Faraday induction. Each sensor then electrically oscillates at a resonant frequency that is dependent upon the capacitance, inductance and resistance of each sensor. The frequency, amplitude and bandwidth of this oscillation are wirelessly sensed by the magnetic field response recorder. The sensor's response is indicative of a parameter that is to be measured.

While the above-described magnetic field response measurement acquisition system greatly improves the state-of-the-art of wireless sensing, electrical connections are still required between the sensor's inductor and capacitor. Such connections are subject to breakage, especially if the sensor will undergo flexing during its useful life.

SUMMARY OF THE INVENTION

Accordingly, it is an object of the present invention to provide a wireless chemical sensor.

Another object of the present invention is to provide a wireless chemical sensor that need not expose any electrical components thereof to a chemical environment being monitored.

Still another object of the present invention is to provide a wireless chemical sensor that minimizes required components in order to minimize failures as well as cost.

Yet another object of the present invention is to provide a wireless chemical sensor that is functional after many types of damaging events.

Other objects and advantages of the present invention will become more obvious hereinafter in the specification and drawings.

In accordance with the present invention, a wireless chemical sensor includes an electrical conductor, a material spaced apart from the electrical conductor, and an electric insulator disposed between the electrical conductor and the material. The electrical conductor has first and second ends and is shaped between the first and second ends for storage of an electric field and a magnetic field. The first and second ends remain electrically unconnected such that the electrical conductor so-shaped defines an unconnected open-circuit having inductance and capacitance. In the presence of a time-varying magnetic field, the electrical conductor so-shaped resonates to generate harmonic electric and magnetic field responses, each of which has a frequency, amplitude and bandwidth associated therewith. The material is spaced apart from the electrical conductor at a location lying within at least one of the electric and magnetic field responses so-generated. The material changes in electrical conductivity in the presence of a chemical-of-interest. The change in conductivity results in a change to the conductor's generated harmonic electric and magnetic field responses.

DETAILED DESCRIPTION OF THE INVENTION

Figure 1:
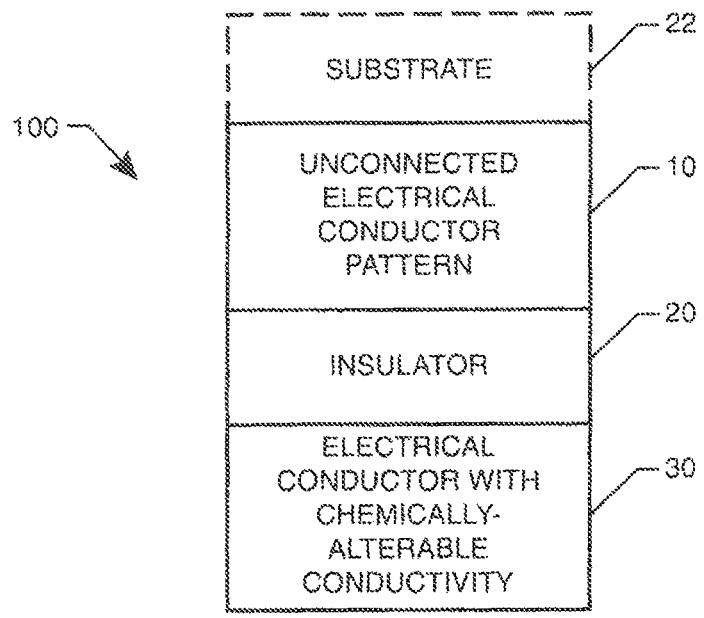
FIG. 1 is a schematic view of a wireless chemical sensor in accordance with an embodiment of the present invention.

Referring now to the drawings and more particularly to FIG. 1, a wireless chemical sensor in accordance with an embodiment of the present invention is shown and is referenced generally by numeral 100. Sensor 100 is constructed to be sensitive to the presence of a chemical-of-interest that can be in the form of a solid, liquid or gas without departing from the scope of the present invention. In the illustrated embodiment, sensor 100 includes an unconnected electrical pattern 10, an electrical insulator 20, and a material 30 whose electrical conductivity is altered (e.g., increased, decreased, reduced to near zero, etc.) when in the presence of a chemical-of-interest (not shown). Accordingly, material 30 is selected to be a material that is initially conductive, partially conductive, or non-conductive, but whose electrical conductivity changes when in the presence of a chemical-of-interest.

As will be explained further below, it is the change in electrical conductivity of material 30 that allows sensor 100 to be sensitive to the chemical-of-interest. Material 30 can be in the form of a sheet spanning the area of pattern 10 and adapted to be mounted where it is needed. However, the present invention is not so limited as material 30 could also be in the form of a thin strip overlaying some region of pattern 10. The change in electrical conductivity of material 30 in the presence of the chemical-of-interest can be caused by a chemical reaction between material 30 and the chemical-of-interest, or absorption of the chemical-of-interest by material 30.

Electric insulator 20 is any material/structure that electrically insulates pattern 10 from material 30 in all operating conditions to include those conditions when the chemical-of-interest is present. Electric insulator 20 can be a structural element/substrate on which pattern 10 and material 30 are mounted such that sensor 100 is a prefabricated sensor with each element thereof being flexible or inflexible to suit a particular application. However, electric insulator 20 can also be a structure inherent in an environment where pattern 10 and material 30 will be installed. For example, if a chemical-of-interest was to be monitored in the air outside of a building, electric insulator 20 could be a window in the building. Material 30 would then be mounted on the outside of the window and pattern 10 would be mounted on the inside of the window opposite material 30. Still further, electric insulator 20 could simply be an air gap disposed between pattern 10 and material 30.

Electrical conductor pattern 10 is any electrical conductor (e.g., wire, run, thin-film trace, etc.) that can be shaped to form an open-circuit pattern that can store an electric field and a magnetic field. The term "open-circuit pattern" as used herein means that the conductor has two ends that are electrically unconnected so that the resulting conductor pattern is an electrical open circuit having inductance and capacitance attributes.

Pattern 10 can be a stand-alone electrically-conductive run. Pattern 10 can also be made from an electrically-conductive run or thin-film trace that can be deposited directly onto insulator 20 or on an optional substrate material 22 (referenced by dashed lines to indicate the optional nature thereof) that is electrically insulating and non-conductive. The particular choice of the substrate material will vary depending on how it is to be attached to insulator 20 or otherwise mounted in its desired location. Although not a requirement of the present invention, the surface on which pattern 10 is deposited is typically a planar surface. Techniques used to deposit pattern 10 either directly onto insulator 20 or on a substrate material can be any conventional metal-conductor deposition process to include thin-film fabrication techniques. As will be explained further below, pattern 10 can be constructed to have a uniform or non-uniform width, and/or uniform or non-uniform spacing between adjacent portions of the pattern's runs/traces.

The basic features of pattern 10 and the principles of operation for sensor 100 will be explained for a spiral-shaped conductor pattern. However, it is to be understood that the present invention could be practiced using other geometrically-patterned conductors provided the pattern has the attributes described herein. The basic features of a spiral-shaped conductor that can function as pattern 10 are described in detail in U.S. Patent Publication No. 2007/0181683, the contents of which are hereby incorporated by reference in their entirety. For purpose of a complete description of the present invention, the relevant portions of this publication will be repeated herein.

As is well known and accepted in the art, a spiral inductor is ideally constructed/configured to minimize parasitic capacitance so as not to influence other electrical components that will be electrically coupled thereto. This is typically achieved by increasing the spacing between adjacent conductive portions or runs of the conductive spiral pattern. However, in the present invention, pattern 10 is constructed/configured to have a relatively large parasitic capacitance. The capacitance of pattern 10 is operatively coupled with the pattern's inductance such that magnetic and electrical energy can be stored and exchanged by the pattern. Since other geometric patterns of a conductor could also provide such a magnetic/electrical energy storage and exchange, it is to be understood that the present invention could be realized using any such geometrically-patterned conductor and is not limited to a spiral-shaped pattern.

The amount of inductance along any portion of a conductive run of pattern 10 is directly related to the length thereof and inversely related to the width thereof. The amount of capacitance between portions of adjacent conductive runs of pattern 10 is directly related to the length by which the runs overlap each other and is inversely related to the spacing between the adjacent conductive runs. The amount of resistance along any portion of a conductive run of pattern 10 is directly related to the length and inversely related to the width of the portion. Total capacitance, total inductance and total resistance for a spiral pattern are determined simply by adding these values from the individual portions of the pattern. The geometries of the various portions of the conductive runs of the pattern can be used to define the pattern's resonant frequency.

Pattern 10 with its inductance operatively coupled to its capacitance defines a magnetic field response sensor. In the presence of a time-varying magnetic field, pattern 10 electrically oscillates at a resonant frequency that is dependent upon the capacitance and inductance of pattern 10. This oscillation occurs as the energy is harmonically transferred between the inductive portion of pattern 10 (as magnetic energy) and the capacitive portion of pattern 10 (as electrical energy). That is, when excited by a time-varying magnetic field, pattern 10 resonates a harmonic electric field and a harmonic magnetic field with each field being defined by a frequency, amplitude, and bandwidth.

Figure 2:
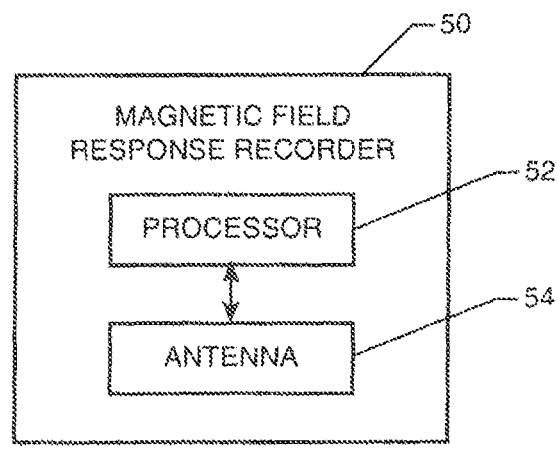
FIG. 2 is a schematic view of a magnetic field response recorder used in an embodiment of the present invention.

The application of a magnetic field to pattern 10, as well as the reading of the induced harmonic response at a resonant frequency, can be accomplished by a magnetic field response recorder. The operating principles and construction details of such a recorder are provided in U.S. Pat. Nos. 7,086,593 and 7,159,774, the contents of which are hereby incorporated by reference in their entirety. Briefly, as shown in FIG. 2, a magnetic field response recorder 50 includes a processor 52 and a broadband radio frequency (RF) antenna 54 capable of transmitting and receiving RF energy. Processor 52 includes algorithms embodied in software for controlling antenna 54 and for analyzing the RF signals received from the magnetic field response sensor defined by pattern 10. On the transmission side, processor 52 modulates an input signal that is then supplied to antenna 54 so that antenna 54 produces either a broadband time-varying magnetic field or a single harmonic field. On the reception side, antenna 54 receives harmonic magnetic responses produced by pattern 10. Antenna 54 can be realized by two separate antennas or a single antenna that is switched between transmission and reception.

In operation, when pattern 10 is exposed to a time-varying magnetic field (e.g., as generated by recorder 50), pattern 10 resonates harmonic electric and magnetic fields. The generated magnetic field is generally spatially larger than the generated electric field. Material 30 is positioned relative to pattern 10 such that it will lie within one or both of the generated magnetic and electric fields. By way of example, the operation of sensor 100 will be described relative to the generated magnetic field emanating from pattern 10 when it is exposed to a time-varying magnetic field.

For fixed excitation conditions, the magnetic field response frequency, amplitude, and bandwidth of pattern 10 are dependent upon the electric conductivity of any material placed within its magnetic field. That is, when a material having electrical conductivity properties (e.g., material 30) is placed inside either the generated magnetic field or electric field of pattern 10, the generated fields around pattern 10 are attenuated more when the conductivity of material 30 increases (after being exposed to the chemical-of-interest) and attenuated less when the conductivity of material 30 decreases (after being exposed to the chemical-of-interest). The energy lost from the generated magnetic field and electric field will alter the magnetic field response frequency, amplitude and bandwidth of pattern 10. More specifically, since there is less energy in the generated magnetic field, pattern 10 exhibits lower inductance and capacitance, and produces a lower response amplitude. Accordingly, if the relative positions of pattern 10 and material 30 remain fixed and if the conductivity of material 30 is fixed, then the magnetic field response of sensor 100 remains unchanged for fixed excitation conditions. These fixed conditions and resulting magnetic field response of sensor 100 define a baseline response for sensor 100 that is recorded prior to using sensor 100.

In accordance with the present invention, material 30 is a conductive material that will experience a change in electrical conductivity in the presence of a chemical-of-interest (e.g., via chemical reaction, chemical absorption, etc.). Accordingly, the above-described baseline response of sensor 100 is recorded in conditions where the chemical-of-interest is not present. Then, when material 30 is subsequently exposed to a chemical-of-interest, its electrical conductivity is altered to thereby change the magnetic field response of sensor 100 in a corresponding fashion. For example, in the case of a sheet of material 30 overlaying pattern 10, if the presence of the chemical-of-interest causes material 30 to become less conductive, pattern 10 will lose less energy resulting in a decreased response in bandwidth, decreased frequency, and increased response in amplitude. Thus, the magnetic field response of sensor 100 can be used to detect the presence of the chemical-of-interest. Once the baseline response of sensor 100 is known and sensor 100 is placed in use, interrogation/monitoring of sensor 100 (for changes in response relative to the baseline response) can be carried out continuously, periodically, on-demand, etc., without departing from the scope of the present invention.

Figure 3:
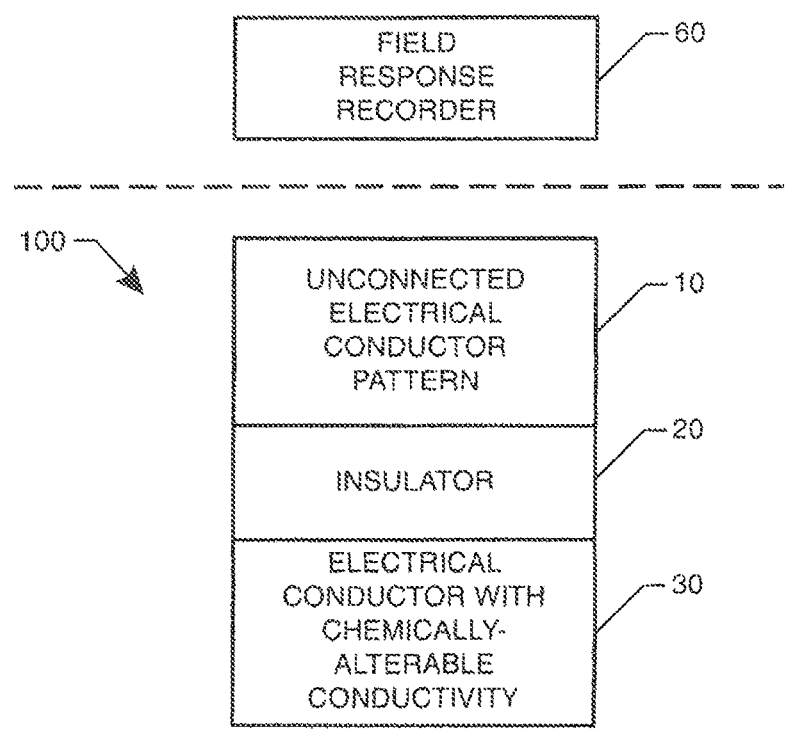
FIG. 3 is a schematic view of a wireless chemical sensor to include a field response recorder in accordance with another embodiment of the present invention.

As mentioned above, a magnetic field response recorder can be used to supply the time-varying magnetic field used to excite pattern 10 and to read/record the generated magnetic field provided by pattern 10. However, the present invention is not so limited since the excitation time-varying magnetic field also causes an electric field to be produced by pattern 10. If material 30 were positioned to lie within the electric and magnetic field responses of pattern 10 (e.g., through proper sizing of insulator 20), one or both of the field responses could be monitored. Accordingly, FIG. 3 illustrates another embodiment of the present invention where pattern 10 of sensor 100 is excited and monitored by a field response recorder 60. Recorder 60 transmits the excitation magnetic field to pattern 10 and monitors one or both of the generated magnetic and electric field responses of pattern 10 if material 30 is located close enough to pattern 10 to lie in both the magnetic and electric field responses. In terms of the electric field response, recorder 60 monitors the frequency, amplitude and bandwidth of the electric field response.

Figure 4:
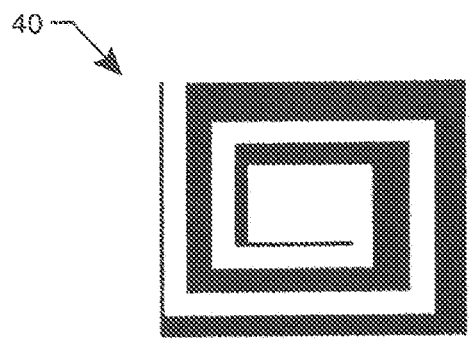
FIG. 4 is a schematic view of a spiral trace conductor pattern whose traces are non-uniform in width.
Figure 5:
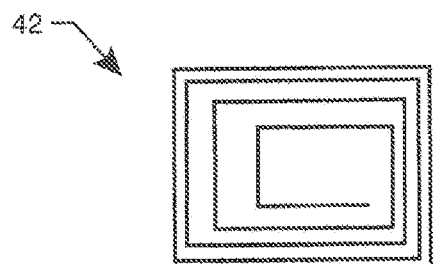
FIG. 5 is a schematic view of a spiral trace conductor pattern having non-uniform spacing between the traces thereof.
Figure 6:
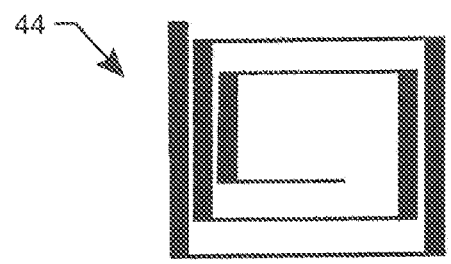
FIG. 6 is a schematic view of a spiral trace conductor pattern having non-uniform trace width and non-uniform trace spacing.

Also as mentioned above, both the width of the pattern's conductive runs/traces and the spacing between adjacent portions of the conductive runs/traces can be uniform. However, the present invention is not so limited. For example, FIG. 4 illustrates a spiral pattern 40 in which the width of the conductive trace is non-uniform while the spacing between adjacent portions of the conductive trace is uniform. FIG. 5 illustrates a spiral pattern 42 in which the width of the conductive trace is uniform, but the spacing between adjacent portions of the conductive trace is non-uniform. Finally, FIG. 6 illustrates a spiral pattern 44 having both a non-uniform width conductive trace and non-uniform spacing between adjacent portions of the conductive trace.

Figure 7:
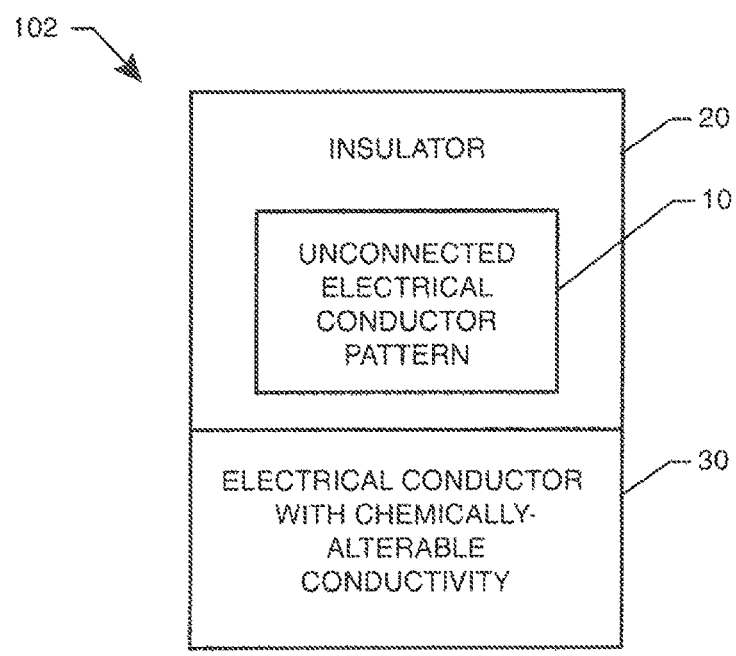
FIG. 7 is a schematic view of a wireless chemical sensor in accordance with another embodiment of the present invention.

The wireless chemical sensor of the present invention can be configured in other ways than described above without departing from the scope of the present invention. For example, FIG. 7 illustrates a sensor 102 in which its unconnected electrical conductor pattern 10 is encased in electric insulator 20. In this embodiment, insulator 20 also protects pattern 10 from environmental conditions. Material 30 can be positioned adjacent to insulator 20 or can be coupled thereto. The operation of sensor 102 is the same as described above.

The present invention is further discussed in Woodard, Olgesby, Taylor and Shams, "Chemical Detection using Electrically Open Circuits having no electrical Connections," IEEE Sensors 2008, 26-29 Oct. 2008, hereby incorporated by reference in its entirety.

The advantages of the present invention are numerous. The wireless chemical sensor requires only a simple unconnected, open-circuit conductor shaped to store electric and magnetic fields, and a material that experiences a change in conductivity in the presence of a chemical-of-interest. The material is simply spaced apart from the shaped conductor by air, some non-conductive structure inherent in the application environment, or by an insulator/substrate that also serves as the means to "package" the shaped conductor to thereby form a prefabricated wireless chemical sensor. The wireless chemical sensor requires no electrically connected components, is simple to produce, and can be excited/powered using known field response recorder technology. The shaped conductor and material can be separated such that only the material need be exposed to a potentially harsh chemical environment.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

The invention claimed is:

1. A wireless chemical sensor, comprising:
an electrically-insulating substrate having opposing faces;
an open-circuit pattern of electrically-conductive material on a first face of said opposing faces of said substrate, said pattern having two electrically unconnected ends, said pattern shaped for storage of an electric field and a magnetic field, said pattern having inductance and capacitance that allows said pattern to generate harmonic electric and magnetic field responses when in the presence of a time-varying magnetic field, each of said electric and magnetic field responses having a frequency, amplitude and bandwidth associated therewith; and
a material on a second face of said opposing faces of said substrate wherein said material lies within at least one of said electric and magnetic field responses so-generated, said material selected to affect attenuation of energy associated with said electric and magnetic field responses so-generated in the presence of a chemical-of-interest.

2. A wireless chemical sensor as in claim 1, further comprising a magnetic field response recorder for wirelessly transmitting said time-varying magnetic field to said pattern and for wirelessly detecting said frequency, amplitude and bandwidth associated with said magnetic field response so-generated.

3. A wireless chemical sensor as in claim 1, further comprising an electric field response recorder for wirelessly transmitting said time-varying magnetic field to said pattern and for wirelessly detecting said frequency, amplitude and bandwidth associated with said electric field response so-generated.

4. A wireless chemical sensor as in claim 1, wherein said substrate is flexible.

5. A wireless chemical sensor as in claim 1, wherein said first face is planar and wherein said pattern is a spiral trace.

6. A wireless chemical sensor as in claim 5, wherein said spiral trace is uniform in width.

7. A wireless chemical sensor as in claim 5, wherein spacing between adjacent portions of said spiral trace is uniform.

8. A wireless chemical sensor as in claim 5, wherein said spiral trace is non-uniform in width.

9. A wireless chemical sensor as in claim 5, wherein spacing between adjacent portions of said spiral trace is non-uniform.

10. A wireless chemical sensor as in claim 1, wherein said material is adapted to chemically react with the chemical-of-interest.

11. A wireless chemical sensor as in claim 1, wherein said material is adapted to absorb the chemical-of-interest.

12. A wireless chemical sensor as in claim 1, wherein said substrate encases said pattern.

* * * * *